United States Patent [19]

Matthews

[11] Patent Number: 5,077,398

[45] Date of Patent: Dec. 31, 1991

[54] PROCESS FOR ISOLATION OF AVERMECTIN B1 COMPONENTS WITH IMPROVED PURITY AND SUBSEQUENT ISOLATON OF B2 COMPONENTS

[75] Inventor: Frank J. Matthews, Edison, N.J.

[73] Assignee: Merck & Co., Inc., Rahway, N.J.

[21] Appl. No.: 931,839

[22] Filed: Nov. 18, 1986

[51] Int. Cl.$^5$ .................................................. C07M 1/00
[52] U.S. Cl. .................................... 536/7.1; 536/16.9; 536/127
[58] Field of Search ...................... 536/7.1, 127, 16.9

[56] References Cited

U.S. PATENT DOCUMENTS

| | | | |
|---|---|---|---|
| 4,130,709 | 12/1978 | Nagarajan | 536/16.8 |
| 4,160,083 | 7/1979 | Cole | 536/7.1 |
| 4,160,084 | 7/1979 | Miller et al. | 536/7.1 |
| 4,160,861 | 7/1979 | Cole et al. | 536/7.1 |
| 4,161,583 | 7/1979 | Wilson et al. | 536/7.1 |
| 4,172,940 | 10/1979 | Chaiet | 536/17 A |
| 4,199,569 | 4/1980 | Chabala et al. | 514/29 |
| 4,248,999 | 2/1981 | Baba et al. | 536/17.4 |
| 4,310,519 | 1/1982 | Albers-Schonberg et al. | 514/29 |
| 4,423,211 | 12/1983 | Bagner et al. | 536/16.9 |

Primary Examiner—Johnnie R. Brown
Assistant Examiner—Elli Peselev
Attorney, Agent, or Firm—David L. Rose; Joseph F. DiPrima

[57] ABSTRACT

This invention relates to a novel process for isolation and purification of avermectin compounds which are produced by the microorganism, *Streptomyces avermitilis*. The process disclosed herein involves two steps, namely, crude crystallization and recrystallization. The isolated compounds are described generically as avermectin B1 and B2 and have significant parasiticidal activity.

16 Claims, No Drawings

PROCESS FOR ISOLATION OF AVERMECTIN B1 COMPONENTS WITH IMPROVED PURITY AND SUBSEQUENT ISOLATON OF B2 COMPONENTS

BACKGROUND OF THE INVENTION

This invention relates to a novel two-step process for isolation and purification of avermectin compounds which are produced by the microorganism, *Streptomyces avermitilis*. The process described herein involves two-steps, namely, crude crystallization of avermectin B1 and crude crystallization of avermectin B2 component from mother liquors obtained from a conventional process for preparation of said avermectin B1 compounds.

DESCRIPTION OF THE PRIOR ART

The avermectins referred to herein are products produced by known fermentation methods, for example, see U.S. Pat. Nos. 4,310,519 and 4,199,569 and extracted from fermentation broth as described in U.S. Pat. No. 4,423,211.

In the past, a four-step process, was used to isolate the B1 components via extraction, concentration, crude crystallization of B1 components and recrystallization of B1 components as shown below:

A) Extraction

The fermentation broth was heat treated at 20° C.-100° C., pH adjusted to 2.5 to 6.0, and extracted with an organic solvent which is immiscible or partially miscible with water. Suitable solvents include toluene, n-butanol, methylene chloride, methyl isobutyl ketone, ethyl acetate, xylene, chlorotoluene, chlorobenzene, etc.

B) Concentration To An Oil

The rich extract wa concentrated until it is approximately 50% (v/v) fermentation oils (lipid and defoamer), and 50% (v/v) solvent. This concentrate was carbon treated and filtered to remove cell debris. The remaining solvent was stripped from the oil by steam distillation, and the oil dried by azeotropic distillation. Low boiling solvents which form azeotropes with water may be used (i.e. hexane, heptane, methylene chloride, benzene, toluene, etc.)

C) CRYSTALLIZATION OF B1 COMPONENTS

The oil from step B was charged to a vessel. Approximately ⅓ volume of a low boiling alcohol (i.e. Methanol, ethanol, isopropanol, n-butanol, etc.) was added to the oil at 70° C. to induce crystallization of avermectin B1. Ethanol is preferred. The batch was cooled and aliphatic hydrocarbons added to improve yield and filtration. The B1 components were present in the oil in concentration of 100 to 150 g/l. The B2 component is present in the oil at concentrations of 70 to 105 g/l. Batch crystallization from high initial concentrations produce fine B1 crystals which are difficult to centrifuge. In addition, B2 frequently crystallizes from high concentrations. Once B2 has crystallized, an additional recrystallization is required to purify the B1 components. Simultaneous precipitation of B1 and B2 compromises the efficiency of the process. An additional recrystallization must be performed when B1 and B2 precipitate simultaneously.

D) RECRYSTALLIZATION OF B1 COMPONENTS

The B1 component was recrystallized from ethanol or other suitable solvents to remove traces of B2. The crude B1 crystals obtained via this procedure are typically 85% B1 components, 9% B2 components and 6% of the other avermectins and related impurities.

The "b" compounds, those with a 25-iso-propyl group are difficult to separate from the corresponding "a" compound with a 25-sec-butyl group and as such the compounds are generally isolated as mixtures of the two compounds. Thus references in the instant application to "a" compounds such as B1a, A1a and the like, are construed to define the pure compound as well as those which actually contain a certain proportion of the corresponding "b" compound. Alternatively, this representation of a mixture is sometimes done by referring to "the B1 or B2 compounds" or by separating the "a" compound from the "b" compound by a slash (/) such as B1a/B1b, B2a/B2b and the like.

In the isolation of the avermectin compounds, which serve as starting materials for the instant processes, from the fermentation broth, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant separation techniques. In particular it may not be necessary to separate the "b" components from the related "a" component. Separation of these closely related compounds is generally not practiced since the "b" compound is present only in a small percent by weight, and the structural differences has negligible effect on physical and chemical processes and biological activities. In particular it has been found that the starting materials for the compounds of this invention are very often prepared in a ratio of about 80% avermectin B1a or B2 a and 20% avermectin B1b or B2b. Thus the preferred composition of this invention is one which contains about 80% of the "a" component and 20% of the "b" component.

SUMMARY OF THE INVENTION

This invention relates to a novel two-step process for isolation and purification via crude crystallization and recrystallization of avermectin components, B1 and B2 from process streams.

Accordingly, it is an object of this invention to provide a novel two-step process for isolation and purification of avermectin components, B1 and B2.

A further object of this invention is to describe the specific conditions and reagents which produce an improved yield and purity of avermectin, B1, a key intermediate for the production of ivermectin.

Another object of the invention is to provide a novel and economical process and conditions which afford isolation and purification of the B2 components via a crystallization process.

These and other objects of the invention will become apparent from the following description.

DESCRIPTION OF THE INVENTION

This invention concerns a novel two-step process for isolation and purification of avermectin compounds. The novel two-step process described herein is disclosed below.

A) Crude Crystallization-B1 Components

The hot (temperature ranges from 50° to 110° C.) oil from conventional step B above was slowly added to the crystallizing solvent at temperatures ranging from 10° to 80° C., preferably at 20° to 60° C. Additionally, the temperature of said crystallizing solvent can range from 10° C. to 50° C. or 10° C. to 30° C. The previously mentioned solvents are applicable, however, alcohols or hydrocarbon/alcohol mixtures are preferred. The addition procedure of the oil to the solvents rather than the solvents to the oil makes it possible to better control the avermectin concentration and degree of super-saturation in the solvent mixture and thereby obtain B1 components with improved purity. B1 seeds were introduced when the solvent mixture is at saturation with respect to the B1 component. The purity of the crude B1 crystals is determined by the concentration of seed in the crystallizer. If 2.0 g/l of seed crystals is charged, the crude B1 crystals will average 90% of B1. If 20 g/l of seed is charged, the crude B1 crystals will average 95-97% B1.

The remaining oil was slowly (2-8 hours) transferred into the crystallizer and the batch cooled slowly to promote crystal growth. Centrifugation and washing of the large B1 crystals was easily accomplished in good yield. In contrast to the prior procedure, the B1 crystals contained 1-2.5% B2 and no additional recrystallization steps were needed to remove B2 components. No B2 seed was introduced during B1 crystallization via the new process, therefore, it is possible to supersaturate B2 in the crude crystallizer. B1 crystals have been centrifuged from mother liquors supersaturated in B2, but B2 can crystallize spontaneously. It is preferable to choose solvent compositions in which the B2 is not saturated. In either case, after the B1 crystals are separated, the mother liquors from B1 centrifugation are sent forward to B2 crystallization.

B) Crude Crystallization B2 Component

The mother liquors from step A can be supersaturated with respect to B2 by
1. concentrating to an oil and adding new solvents.
2. adding solvents without any further concentration
or
3. lowering the temperature.

B2 can be crystallized from supersaturated mother liquors by the introduction of B2 seed. Alternatively, B2 supersaturation can be increased until B2 nucleates spontaneously. The novel process thus involves isolation of crude avermectin B1 of improved purity and the further benefit that avermectin B2 is separately isolated which was not possible with the prior art process. Previously, the B2 components were unrecoverable in a pure state and were discarded. The new process originates with the hot oils (temperature ranging from 50° to 110° C.) from step B of the conventional process. Said oil was slowly added to a crystallizing solvent such as alcohols or hydrocarbon/alcohol mixtures. Representative solvents suitable for use herein are aliphatic hydrocarbons, such as hexane, heptane, octane, and the like; aromatic hydrocarbons such as benzene and totuene; and the C1-C4 alcohols such as methanol, ethanol, n-butanol and the like: preferably hexane/ethanol at temperatures ranging from 30° to 100° C., preferably 40° to 60° C.; wherein the hydrocarbon constitutes from 50 to 90% of the solvent mixture. B1 seeds are introduced at low concentrations to initiate crystallization but preferably at high concentrations to promote growth as opposed to nucleation. High concentrations of seed allow crude material of high purity to be produced. In many cases recrystallization of the B1 components are not necessary. The B1 crystals are then filtered from the mother liquor.

The B2 component remains uneffected and may be crystallized from the mother liquor by seeding with B2 crystals or optionally by supersaturating the mother liquors via increasing B2 concentration, altering the solvent composition, or reducing the temperature and then seeding with B2 to obtain crystallization. Another novel feature of this invention is that B1 and B2 components can be crystallized from the same mother liquors.

The following examples illustrate the process described herein for isolation and purification of avermectin B1 and B2 components. The examples should be construed as an illustration of the invention rather than a limitation thereof.

EXAMPLE 1

Crystallization of B1 Component

A sample of fermentation oils was prepared via the conventional process. The oils assayed 159.4 g B1 /l and 107.0 g B2/l. The laboratory crystallizer was a 500 cc round bottomed flask equipped with agitator, heating mantle, condenser, thermometer and a jacketed dropping funnel set so that hot oil could be added to the 500 cc flask by gravity. 91.6 g of oil were charged to the dropping funnel and heated to 80°. 210 cc of 85/15 (v/v) hexane/ethanol were charged to the 500 cc flask and heated to 50° C. 8.8 g of oil were added to the hot solvent with a syringe to attain B1 supersaturation. 0.2 g of pure B1 (~0.9 g seed/l) was added to the solvent as seed and additional crystals nucleated immediately. The batch was aged one hour at 50° C. and the remaining oil was added to the solvent over 27 hours. The batch was aged at 50° C. for 1 hour and then cooled over 3 hours to 20° and then aged overnight at 20° C. The batch was filtered at 20–22° C. The crystals were washed with 85/15 (v/v) hexane/ethanol and vacuum dried. The in-hand yield of B1 was 81.4%. The mother liquors contained 38.3 g/l B2 or 77.4% of the B2 in the conventional oil. The Purity of the crude B1 was 92.3%.

| Mass Balances: | Crystallization of B1 | | |
|---|---|---|---|
| oil: | 0.1004 l | @ 159.4 g B1/l | = 16 g B1 |
| | | @ 107.0 g B2/l | = 10.7 g B2 |
| mother liquors: | 0.217 l | @ 5.42 g/l B1 | = 1.18 g B1 |
| | | @ 38.3 g/l B2 | = 8.31 g B2 |
| wash: | 0.167 l | @ 2.896 g/l B1 | = 0.484 g B1 |
| | | @ 8.10 g/l B2 | = 1.35 g B2 |
| cake: | 14.71 g | @ 92.3% B1, 4.04% LOD | = 13.02 g B1 |
| | | @ 6.1% B2, 4.04% LOD | = 0.86 g B2 |

In-hand yield of B1 = 81.4%
B2 retained in mother liquors = 77.4%
B1 mass balance = 91.2%
B2 mass balance = 97.9%

Crystallization of B2 Component

Crude mother liquors were obtained and assayed at 28.2 g/l B2. Two liters of these mother liquors were vacuum concentrated to an oil. Then, the total volume was adjusted to two liters with 70/30 (v/v) hexane/ethanol. This concentration was performed to remove water. The dried mother liquors were charged to a two liter resin kettle equipped with an agitator, thermometer and condenser. The batch was cooled at 0° and 0.2 g of B2 seed was added. The batch was then aged 24 hours at 0° C. The batch was then filtered on a Buchner funnel. The cake was transferred to a beaker and reslurried with 90 cc of 85/15 hexane/ethanol. This was filtered and reslurried a second time with 85/15 wash. This was filtered and the cake given a 90 cc 85/15 hexane/ethanol direct wash and dried. The in-hand yield was 36.4%. The B2 yield can be improved by altering the mother liquor composition in accordance with solubility data.

TABLE 1

Mass Balance for Lab Crystallization of B2

Feed: $2.0 \, l \, @ \, 31.3 \frac{g. \, B2}{l} = 62.6 \, g. \, B2$

Cake: 24.7 g. @ 2.94% LOD and 95.2% B2 = 22.8 g. B2
Wash: 0.284 l @ 13.46 g B2/l = 3.8 g. B2

Crude ML $1.78 \, l \, @ \, 17.57 \frac{g. \, B2}{2} = 31.3 \, g. \, B2$

B2 Mass Balance = 92.5%

EXAMPLE 2

A sample of fermentation oils was prepared and assayed 110.2 g B1/l and 80.2 g B2/l. The laboratory crystallizer was the same as used in Example 1. 130 cc of 50/50 (v/v) hexane/ethanol was charged to the 500 cc flask. 100 g of oil was charged to the jacketed dropping funnel. 40 cc of oil at 80° was added to the solvents at 50° and seeded with 10.99 g ( 64.6 g/l) of pure B1 component. The remaining oil was charged to the crystallizer over 4 hours and the batch cooled to 10° over a period of 8 hours. The final purity of the precipitated B1 was 95.9% at a yield of 87.4%.

Now having described the invention there will become evident varients which are obvious to one skilled in the art, which varients do not depart from the spirit of the following claims.

What is claimed is:

1. A process for isolation of avermectin B1 components with improved purity from concentrated hot oil consisting of approximately 50% lipid and defoamer and 50% organic solvent containing both B1 and B2 components in concentrations of about 100 to 150 g/l of B1 components and 70 to 105 g/l of B2 components having a temperature ranging from 50° to 110° C. which comprises the steps of:
   A) adding the hot oil to a crystallizing solvent mixture of a hydrocarbon selected from the group consisting of hexane, heptane, pentane, benzene and toluene and an alcohol selected from the group consisting of methanol ethanol, isopropanol, n-butanol, isobutanol and n-propanol and lowering the temperature within the range of 10°-80° C., and
   B) seeding the mixture with B1 crystals and isolating the B1 crystals and substantially retaining the B2 in the mother liquors.

2. The process of claim 1, wherein in Step A, the crystallizing solvent is a hydrocarbon and alcohol mixture wherein said hydrocarbon constitutes from 50 to 90% of said crystallizing solvent and the temperature ranges from 20° to 60° C.

3. The process of claim 1, wherein said crystallizing solvent is a mixture of hexane/ethanol and the ratio of hexane/ethanol is 75-85:25-15.

4. The process of claim 3, wherein the ratio is 80:20.

5. The process of claim 1, wherein said crystallizing solvent is benzene/ethanol and said temperature ranges from 10° to 30° C.

6. The process of claim 5, wherein the ratio of benzene/ethanol is 75-85:25-15.

7. The process of claim 6, wherein the ratio is 80:20.

8. The process of claim 1, wherein said crystallizing solvent is a mixture of hexane/isobutanol, isopropanol or n-butanol and said temperature ranges from 10° to 50° C.

9. A process for isolation of avermectin B2 components with improved purity from concentrated hot oil consisting of approximately 50% lipid and defoamer and 50% organic solvents containing both B1 and B2 components in concentrations of about 100 to 150 g/l of B1 components and 70 to 105 g/l of B2 components having a temperature ranging from 50° to 110° C. and subsequent isolation of B2 components from other liquors which comprises the steps of:
   A) adding the hot oil to a crystallizing solvent mixture of a hydrocarbon selected from the group consisting of hexane, heptane, pentane, benzene and toluene and an alcohol selected from the group consisting of methanol, ethanol, isopropanol, n-butanol, isobutanol and n-propanol, and lowering the temperature within the range of 10°-80° C.,
   B) seeding the mixture with B1 crystals and isolating and B1 crystals and substantially retaining the B2 in the mother liquor and
   C) crystallizing the B2 from the mother liquors of Step B by (1) A and B above, seeding with B2; (2) adding additional solvent mixture to the point of spontaneous crystallization of B2 or crystallization by B2 seeds; or (3) lowering the temperature of B2 or crystallization by B2 seeds.

10. The process of claim 9, wherein in Step a, the crystallizing solvent is a hydrocarbon, alcohol mixture wherein said hydrocarbon constitutes from 50 to 90% of said crystallizing solvent and the temperature ranges from 20° to 60° C.

11. The process of claim 9, wherein said crystallizing solvent is a mixture of hexane/ethanol and the ratio of hexane/ethanol is 75-85:25-15.

12. The process of claim 11, where the ratio is 80:20.

13. The process of claim 9, wherein said crystallizing solvent is benzene/ethanol and said temperature ranges from 10° to 30° C.

14. The process of claim 13, wherein the ratio of benzene/ethanol is 75-85:25-15.

15. The process of claim 14, wherein the ratio is 80:20.

16. The process of claim 9, wherein said crystallizing solvent is a mixture of hexane isobutanol, isopropanol or n-butanol and said temperature ranges from 10° to 50° C.

* * * * *